United States Patent [19]

Roberts

[11] Patent Number: 5,447,715

[45] Date of Patent: Sep. 5, 1995

[54] NON-AQUEOUS SUNCARE COMPOSITIONS HAVING HIGH SPF VALUES

[75] Inventor: Richard L. Roberts, Germantown, Tenn.

[73] Assignee: Scholl Inc., Memphis, Tenn.

[21] Appl. No.: 124,257

[22] Filed: May 17, 1989

Related U.S. Application Data

[63] Continuation of Ser. No. 34,113, Apr. 1, 1987, abandoned.

[51] Int. Cl.⁶ .......................... A61K 7/42; A61K 7/44; A61K 7/48; A61K 9/10
[52] U.S. Cl. .................. 424/59; 424/DIG. 5; 424/60; 514/938; 514/944
[58] Field of Search ................... 424/59, 60

[56] References Cited

U.S. PATENT DOCUMENTS

| | | | |
|---|---|---|---|
| 2,770,631 | 11/1956 | Merker | 424/59 X |
| 2,853,423 | 9/1958 | La Via | 424/60 |
| 2,928,858 | 3/1960 | Morehouse | 424/59 X |
| 2,974,089 | 3/1961 | Alexander et al. | 424/60 |
| 3,185,627 | 5/1965 | Kass | 424/59 |
| 4,355,046 | 10/1982 | Süess | 424/355 |
| 4,559,225 | 12/1985 | Fourman | 424/59 |
| 4,663,155 | 3/1987 | Murray et al. | 514/873 |

FOREIGN PATENT DOCUMENTS

| | | | |
|---|---|---|---|
| 1199928 | 9/1965 | Germany | 424/60 |
| 1717102 | 12/1972 | Germany | 424/60 |

OTHER PUBLICATIONS

DiSapio, "Silicones as Adjuvants in Sun Products", Mar. 1987, Cosm. & Toiletries, vol. 102, pp. 102–106.

*Primary Examiner*—Dale R. Ore
*Attorney, Agent, or Firm*—Thomas D. Hoffman; Eric S. Dicker; Robert A. Franks

[57] ABSTRACT

Non-aqueous sunscreen compositions containing an amount of a volatile silicone oil sufficient to maintain the SPF of the waterproof composition at a value greater than about 20 and a conventional non-aqueous sunscreen formulation or a conventional non-aqueous waterproof sunscreen formulation.

17 Claims, No Drawings

NON-AQUEOUS SUNCARE COMPOSITIONS HAVING HIGH SPF VALUES

This is a continuation of application Ser. No. 34,113 filed Apr. 1, 1987, now abandoned.

BACKGROUND OF THE INVENTION

This invention relates to non-aqueous sunscreen compositions having an amount of a volatile silicone oil sufficient to maintain the sun protection factor (SPF) of the compositions at a value greater than about 20.

The sun protection factor (SPF) is a measure of the protection from the sun afforded by a sunscreen agent or composition containing same; compositions having higher SPF values afford more sun protection and are preferred. M. G. deNavarre discloses that small amounts (0.1 to 5 weight percent) of silicone oils can be used in suntan oils to make the oil film formed on the skin more water repellent. See for example The Chemistry and Manufacture of Cosmetics, 2nd Ed., 1975, Vol. III, Chapter 22, pp. 330 and 351 and Vol. IV, Chapter 39, pp. 667 and 668, Continental Press, Orlando, Fla. However, there is no disclosure by deNavarre of any effect silicone oils may have on enhancing the SPF value of the suntan composition. U.S. Patent 4,559,225 (R. G. Fourman) discloses waterproof sunscreen composition having SPF values from 2 to 20. While the sunscreen compositions disclosed by Fourman contain volatile silicon oils, use of a film-forming cellulosic polymer in amounts ranging from 0.10% to 10.0% and a solvent such as an aliphatic alcohol for the cellulosic polymer in the range of 10% to 90.0% of the total composition are required to produce the waterproof sunscreen composition. Westwood Pharmaceutical sells a Presun SPF-29 UV-A/UV-B waterproof sunscreen product. The Westwood Pharmaceutical product is an emulsion product which does not contain any para-aminobenzoates (PABA) UV-B type sunscreening agents. There is still a need for non-emulsion non-aqueous sunscreen composition having a high SPF value, i.e. a value greater than about 20, which may contain a wide range of UV-A and UV-B type (including PABA type) sunscreening agents. There is also a need for non-emulsion non-aqueous waterproof sunscreen composition having a high SPF value.

SUMMARY OF THE INVENTION

The present invention provides a non-aqueous sunscreen composition having a high SPF value comprising (a) an effective amount of a volatile silicone oil sufficient to maintain the SPF of said sunscreen composition at a value greater than about 20 and (b) a conventional non-aqueous sunscreen formulation.

The present invention also provides a nonaqueous waterproof sunscreen composition having a high SPF value comprising (a) an effective amount of a volatile silicone oil sufficient to maintain the SPF of said sunscreen composition at a value greater than about 20 and (b) a conventional non-aqueous waterproof sunscreen formulation.

DETAILED DESCRIPTION OF THE INVENTION

Conventional non-aqueous sunscreen formulation contain at least one cosmetic emollient, at least one cosmetic wax, and at least one sunscreening agent but is substantially free (i.e. contains less than about 0.1%) of film-forming cellulosic polymers such as cellulose ethyl ether and contains less than 10% (by weight) of solvents for such cellulosic polymers i.e., aliphatic alcoholic solvents such as ethanol or isopropanol. By including into such conventional non-aqueous sunscreen formulations a waterproofing effective amount of at least one waterproofing agent, a conventional non-aqueous waterproof sunscreen formulation is formed without the need of a film-forming cellulosic polymer or solvent therefor. We have discovered that by including in conventional non-aqueous sunscreen formulations or conventional non-aqueous waterproof sunscreen formulations an effective amount of a volatile silicone oil, there is obtained a non-aqueous sunscreen composition or non-aqueous waterproof sunscreen composition having a SPF value greater than about 20. The silicone oil is used in place of at least a portion of one of the conventional cosmetic emollients, e.g. petrolatum or mineral oil. Thus, we have also discovered that the volatile silicon oils useful in the compositions of the present invention function as a SPF enhancing factor as well as a cosmetic emollient without the need for the prior art film-forming cellulosic polymer or aliphatic alcoholic solvent therefor.

As used herein in reference to the sunscreen compositions of the present invention, the term "effective amount of a volatile silicon oil" means about 20 to about 40 weight percent, preferably about 22-36 weight percent and more preferably about 22 to about 25 weight percent or more preferably about 34 to about 36 weight percent of the total sunscreen composition. Compositions of the present invention containing the more preferred ranges of about 22 to about 25 weight percent and about 34 to about 36 weight percent of a volatile silicone oil have been found to be surprisingly effective sunscreen compositions.

As used herein, the term "volatile silicone oil" means a silicone oil having a low heat of vaporization, i.e. normally less than about 50 cal per gram of silicon oil.

As used herein in reference to the compositions of the present invention, the term "non-aqueous" means substantially water-free. While water is not intentionally added to the compositions of the present invention, no attempt has been made to exclude or remove water from the ingredients used in the compositions of the present invention since it is not necessary that the compositions of present invention be completely anhydrous.

As used herein in reference to the compositions of the present invention, the term "waterproof" means a composition that remains on the skin after exposure to circulating water for at least 80 minutes using the procedures described in "Sunscreen Drug Products for OTC Human Use", Federal Register, Vol. 43, Aug. 25, 1978, Part 2, pp 38206–38269.

As used herein in reference to the compositions of the present invention, the term "SPF" or "Sun Protection Factor" is defined in the Federal Register, Vol. 43, Aug. 25, 1978 Part 2, at page 38262, col. 1.

The non-aqueous compositions of the present invention contain conventional amounts of one or more cosmetic waxes, cosmetic emollients, and sunscreening effective amount of at least one sunscreening agent and an effective amount volatile silicone oil. The non-aqueous waterproof composition of the present invention include the ingredients in the non-aqueous composition as well as a waterproofing effective amount at least one waterproofing agent.

By the term "waterproofing effective amount of at least one waterproofing agent" means the waterproofing agent(s) is present in the compositions of the present invention at a concentration of about 0.01 to about 5.0 weight percent, preferably about 0.3 to about 3.0 percent.

Typical suitable waterproofing agents include copolymers derived from polymerization of octadecene-1 and maleic anhydride in accordance with the published procedures such as those in U.S. Pat. No. 3,860,700 and U.S. Pat. No. 28,475. The preferred waterproofing agent is a copolymer commercially available from Chevron Chemicals Co. under the tradename, PA-18 polyanhydride resin.

Typical suitable cosmetic waxes include ozokerite, lanolin alcohol, paraffin wax, bayberry wax, polyethylene wax, such as AC polyethylene wax, especially AC 617 available from Allied-Signal Corp., Morristown, N.J.; Polawax (a reaction product of higher fatty alcohols and ethylene oxide available from. Croda, Inc., New York, N.Y. 10016), trihydroxystearin, lanolin wax, beeswax, Candellila wax, microcrystalline wax, Carnauba wax, cetyl alcohol, stearyl alcohol, spermaceti, cocoa butter, fatty acids of lanolin, mono-, di- and triglycerides which are solid at 25° C., e.g., glyceryl tribehenate (a triester of behenic acid and glycerine) and $C_{18}$-$C_{36}$ acid triglyceride, (a mixture of triesters of $C_{18}$-$C_{36}$ carboxylic acids and glycerine) available from Croda, Inc., New York, N.Y. under the tradenames Syncrowax HRC and Syncrowax HGL-C, respectively, fatty esters which are solid at 25° C., silicone waxes such as methyloctadecaneoxypolysiloxane and poly (dimethylsiloxy) stearoxysiloxane, stearyl mono- and diethanolamide, rosin and its derivatives such as the abietates of glycol and glycerol, hydrogenated oils solid at 25° C., and sucroglycerides.

Typical suitable volatile silicone oils include cyclomethicones such as Dow Corning 344 Fluid, Dow Corning 345 Fluid, Dow Corning 244 Fluid and Dow Corning 245 Fluid; as well as Volatile Silicon 7207, a trademark of Union Carbide Corp., Danbury, Conn., low viscosity dimethicones i.e. dimethicones having a viscosity of about 50 cst or less especially dimethicones, such as, Dow Corning 200-0.5 cst Fluid. The Dow Corning Fluids are available from Dow Corning Corporation, Midland, Mich. 48640. Cyclomethicone and dimethicone are names given by the Third Edition of the CTFA Cosmetic Ingredient Dictionary to cyclic dimethyl polysiloxane compounds and a mixture of fully methylated linear siloxane polymers end-blocked with trimethylsiloxy units, respectively. Other volatile silicone oils having a low heat of vaporization, such as those available from General Electric Co., Silicone Products Div., Waterford, N.Y. and SWS Silicones Div. of Stauffer Chemical Co., Adrian, Mich., can also be used in the compositions of the invention.

Typical suitable cosmetic emollients include mineral oil, especially mineral oils having a viscosity in the range of 50 to 500 SUS, lanolin oil, coconut oil, cocoa butter, olive oil, almond oil, macadamia nut oil, aloe extract, jojoba oil, safflower oil, corn oil, liquid lanolin, cottonseed oil and peanut oil.

Other typical suitable cosmetic emollients include Purcellin oil, perhydrosqualene, castor oil, polybutene, odorless mineral spirits, sweet almond oil, avocado oil, calophyllum oil, ricin oil, vitamin E acetate, olive oil, mineral spirits, linolenic alcohol, oleyl alcohol, the oil of cereal germs such as the oil of wheat germ, isopropyl palmitate, isopropyl myristate, butyl myristate, hexadecyl stearate, butyl stearate, decyl oleate, acetyl glycerides, the octanoates and benzoates of ($C_{12}$-$C_{15}$) alcohols, the octanoates and decanoates of alcohols and polyalcohols such as those of glycol and glycerol, ricin oleates of alcohols and poly alcohols such as those of isopropyl adipate, hexyl laurate and octyl dodecanoate.

Other typical suitable cosmetic emollients which are solids or semi-solids at ambient temperatures may be used if admixed with one or more of the cosmetic emollients listed above, in amounts sufficient to provide liquid topical compositions. Such solid or semi-solid cosmetic emollients include hydrogenated lanolin, hydroxylated lanolin, acetylated lanolin, petrolatum, isopropyl lanolate, cetyl myristate, myristyl myristate, myristyl lactate, cetyl alcohol, isostearyl alcohol and isocetyl lanolate.

The compositions of the present invention all contain a sunscreening effective amount of one of an oil-soluble sunscreening agent of the UV-B type or a combination of the UV-B and UV-A types. UV-A type sunscreening agents protect against long wavelength actinic radiation in the 320 to 400 nm range and UV-B sunscreening agents protect against shorter wave length, actinic radiation in the 290-320 nm range.

Typical suitable UV-B type sunscreening agents include substituted para-aminobenzoates, e.g., octyl dimethyl PABA, available from Van Dyk & Co., Inc., Belleville, N.J. 07109 under the tradename Escalol 507 and usually present in the range of about 1.5 to 8.0 weight percent, alkyl esters of para-methoxycinnamate, e.g., octyl para-methoxycinnamate, available from Givaudan Corp., Clifton, N.J. 07104 under the tradename Parsol MCX and usually present in the range of about 1.5-7.5 weight percent, certain esters of salicylic acid, e.g., homomenthyl salicylate, usually in the range of about 4.0 to 15 weight percent or octyl salicylate, usually in the range of about 3 to 5 weight percent. (All weight percents are weight percent of total sunscreen composition).

Typical suitable UV-A type sunscreening agents include benzophenone-3 usually present in the composition in the range of about 0.5 to 6 percent and available from American Cyanamid Co., Wayne, N.J. 07470 under the tradename Spectra-Sorb UV-9 and benzophenone-8, usually present in the composition in the range of about 0.5 to 3 weight percent and available from American Cyanamid Co. under the tradename Spectra-Sorb UV-24 and menthyl anthranilate, usually present in the composition in the range of about 3.5 to about 5.0 weight percent and available from Felfon International, Inc. Brooklyn, N.J. under the tradename Sunarome UVA.

The compositions of the present invention preferably contain at least two UV-B type sunscreening agents or a combination of two UV-B type and one UV-A type sunscreening agent.

The compositions of the present invention may also contain perfumes, preservatives, dyes, softeners, physical reflectors and antioxidants as well as any other class of materials whose presence may be cosmetically, or otherwise desirable.

Typical suitable antioxidants include propyl, octyl and dodecyl esters of gallic acid, butylated hydroxyanisole (usually as a mixture of ortho and meta isomers), butylated hydroxytoluene and nordihydroguaiaretic acid.

Typical suitable preservatives include the lower alkyl esters of para-hydroxybenzoates (parabens) especially, methyl paraben, ethyl paraben, propyl paraben, butyl paraben, isobutyl paraben and mixtures thereof, and benzoic acid.

Typical suitable perfumes include any oil soluble perfume or fragrance or mixture of perfumes or fragrances well known to those skilled in the art.

Typical suitable physical reflectors include talc, kaolin, chalk, precipitated silica, zinc oxide and titanium dioxide.

The compositions of the present invention may be in the form of a liquid, gel or semi-solid preferably a gel or a semi-solid, more preferably a semi-solid, as specified in Example Nos. 1 and 8. The selection of ingredient type and amount is dictated by the nature of the composition, i.e. gel or semi-solid and is within the skill of the cosmetic chemists. Thus larger amounts of cosmetic wax are incorporated into the semi-solid compositions of the present invention than into the liquid ones.

Definitions and suppliers of the ingredients used in the following illustrative examples may be found in the CTFA Cosmetic Ingredient Dictionary, published by the Cosmetic, Toiletry and Fragrance Association, Inc., 1110 Vermont Avenue, NW, Washington, D.C. 20005, Third Edition, 1982. All proportions are by percent weight.

EXAMPLE 1

Semi-Solid Stick Formulation

|  | weight percent |
|---|---|
| Part A |  |
| Ozokerite Wax | 18.50 |
| Lauryl Lactate | 5.00 |
| Microcrystalline Wax | 1.00 |
| Carnauba Wax | 0.50 |
| Polybutene | 17.50 |
| Octyl Methoxycinnamate | 7.50 |
| Octyl Dimethyl PABA | 5.00 |
| Benzophenone-3 | 4.00 |
| Benzoic Acid | 0.20 |
| Propyl Paraben | 0.10 |
| Part B |  |
| Octadecene-1/Maleic Anhydride Copolymer | 1.00 |
| Part C |  |
| Talc | 4.00 |
| Fragrance | 0.05 |
| Part D |  |
| Dow Corning 344 Fluid | 35.65 |
| Total: | 100.00 |

Add all the ingredients in Part A to a pot maintained at a temperature of 80° C. to 82° C. and stir until a homogeneous mixture is formed. Add the ingredient in Part B to the so-formed stirred mixture while maintaining the temperature at a about 82° C. Add thereto the ingredients in Part C and continue to stir while allowing the stirred mixture to cool. At 75° C., add thereto, the ingredient in Part D and stir until a homogeneous mixture is formed. Pour the so-formed mixture into molds.

The semi-solid sunscreen composition of Example 1 was determined to be a waterproof SPF 25 product when tested on human subjects in accordance with the procedures for evaluating SPF static and SPF waterproof II values published in The Federal Register, Vol. 43, Aug. 25, 1978, Part 2, pp 38259 to 38264, inclusive. The following results were obtained:

SPF (static)=25.35±3.66
SPF (waterproof)=24.65±4.41

EXAMPLE 2 and 3

|  | Example 2 weight % | Example 3 weight % |
|---|---|---|
| Part A |  |  |
| Ozokerite Wax | 17.50 | 18.00 |
| Lauryl Lactate | 5.00 | 5.00 |
| Microcrystalline Wax | 1.00 | 1.00 |
| Polybutene | 20.00 | 18.00 |
| Carnauba Wax | — | 0.50 |
| Octyl Methoxycinnamate | 7.50 | 7.50 |
| Octyl Dimethyl PABA | 4.00 | 4.00 |
| Benzophenone-3 | 4.00 | 4.00 |
| Benzoic Acid | 0.20 | 0.20 |
| Propyl Paraben | 0.10 | 0.10 |
| Part B |  |  |
| Octadecene-1/Maleic Anhydride Copolymer | — | 1.00 |
| Part C |  |  |
| Talc | 4.00 | 4.00 |
| Part D |  |  |
| Dow Corning 344 Fluid | 36.70 | 36.70 |
| TOTAL | 100.00 | 100.00 |

The semi-solid sunscreen composition of Examples 2 and 3 were prepared on accordance with the procedure of Example 1 and were determined to be waterproof SPF 21 and 23 products, respectively. When each was tested on human subjects in accordance with the procedures used to evaluate the product of Example 1, the following results were obtained:

| Sunscreen Product | SPF (static) | SPF (waterproof) |
|---|---|---|
| Example 2 | 27.07 ± 3.35 | 20.93 ± 2.49 |
| Example 3 | 26.10 ± 3.18 | 23.20 ± 0.0 |

EXAMPLE 4–7

|  | EXAMPLE NO. | | | |
|---|---|---|---|---|
|  | 4 | 5 | 6 | 7 |
| Part A |  |  |  |  |
| Ozokerite Wax | 17.50 | 18.50 | 18.50 | 18.50 |
| Lauryl Lactate | 5.00 | 5.00 | 5.00 | 5.00 |
| Microcrystalline Wax | 1.00 | 1.00 | 1.00 | 1.00 |
| Polybutene | 20.00 | 17.50 | 17.50 | 17.50 |
| Carnauba Wax | 0.50 | 0.50 | 0.50 | 0.50 |
| Octyl Methoxycinnamate | 7.50 | 7.50 | 7.50 | 7.50 |
| Octyl Dimethyl PABA | 5.00 | 4.00 | 5.00 | 5.00 |
| Benzophenone-3 | — | 4.00 | 4.00 | 4.00 |
| Homomenthyl Salicylate | 10.00 | — | — | — |
| Benzoic Acid | 0.20 | 0.20 | 0.20 | 0.20 |
| Propyl Paraben | 0.10 | 0.10 | 0.10 | 0.10 |
| Part B |  |  |  |  |
| Octadecene-1/Maleic Anhydride Copolymer | — | 1.00 | 1.00 | 1.00 |
| Part C |  |  |  |  |
| Titanium Dioxide | 1.00 | — | — | — |
| Talc | 3.00 | 4.00 | 4.00 | 4.00 |
| Fragrance | — | — | 0.05 | 0.05 |
| Part D |  |  |  |  |
| Dow Corning 344 Fluid | 30.70 | 36.70 | — | 26.65 |
| Dow Corning 345 Fluid | — | — | 35.65 | — |
| Petrolatum | — | — | — | 9.00 |
| TOTAL | 100.00 | 100.00 | 100.00 | 100.00 |

The composition of Examples 4–7 were prepared in accordance with the procedure of Example 1.

When each was tested on human subjects in accordance with procedure of Example #1 the following results were obtained:

| Composition of Example No. | SPF (Static) |
|---|---|
| 4 | 27.07 ± 3.35 |
| 5 | 21.23 ± 2.63 |
| 6 | 17.73 ± 2.19 |
| 7 | 18.99 ± 0.0 |

EXAMPLE 8

| Semi-Solid Stick Formulation | |
|---|---|
| | weight percent |
| Part A | |
| Ozokerite Wax | 17.50 |
| ($C_{12}$-$C_{15}$) Alcohols Benzoate | 5.00 |
| Microcrystalline Wax | 1.00 |
| Polybutene | 20.00 |
| Octyl Methoxycinnamate | 7.50 |
| Homomenthyl Salicylate | 8.00 |
| Benzophenone-3 | 6.00 |
| Menthyl Anthranilate | 3.50 |
| Benzoic Acid | 0.20 |
| Propyl Paraben | 0.10 |
| Part B | |
| Octadecene-1/Maleic Anhydride Copolymer | 2.00 |
| Part C | |
| Polyethylene | 1.00 |
| Part D | |
| Talc | 4.00 |
| Part E | |
| Dow Corning 344 Fluid | 24.20 |
| TOTAL: | 100.00 |

The composition of this Example was prepared in accordance with the procedure of Example 1 except that the polyethylene (ingredient in Part C) is added to a homogeneous mixture of A and B at 80°–82° C. Add thereto talc (the ingredient in Part D) and continue to stir while allowing the stirred mixture to cool. At 75° C., add thereto the Dow Corning 344 Fluid and stir until a homogeneous mixture is formed. Pour the so-formed mixture into molds. The semi-solid sunscreen composition of this Example (#8) was tested on human subjects in accordance with the procedure of Example #1 and the SPF (Static) was determined to be 26.20±4.11.

What is claimed is:

1. A non-aqueous sunscreen composition having a high SPF value comprising (a) an effective amount of a volatile silicone oil having a viscosity of no more than about 50 cst in the range of about 20 to 40 weight percent of the composition sufficient to maintain the SPF of the composition at a value greater than about 20 and (b) a non-aqueous sunscreen formulation containing at least one cosmetic emollient, at least one cosmetic wax and an effective sunscreening amount of at least one sunscreening agent and being substantially free of film-forming cellulosic polymers.

2. A composition of claim 1 wherein the effective amount of volatile silicone oil is about 22 to about 25 weight percent of the composition.

3. A composition of claim 1 wherein the effective amount of the volatile silicone oil is about 34 to about 36 weight percent of the composition.

4. A composition of claim 1 which is a liquid.

5. A compoisiton of claim 1 which is a gel.

6. A composition of claim 1 which is a semi-solid.

7. A non-aqueous waterproof sunscreen composition having a high SPF value comprising (a) an effective amount of a volatile silicone oil having a viscosity of no more than about 50 cst in the range of about 20 to about 40 weight percent of the composition sufficient to maintain the SPF of the composition at a value greater than about 20 and (b) a non-aqueous waterproof sunscreen formulation containing a waterproofing effective amount of a waterproofing agent, at least one cosmetic emollient, at least one cosmetic wax and an effective sunscreening amount of at least one sunscreening agent and being substantially free of film-forming cellulosic polymers.

8. The composition of claim 7 wherein the waterproofing agent is octadecene-1/maleic anhydride copolymer.

9. A composition of claim 7 wherein the effective amount of a volatile silicone oil is about 22 to about 36 weight percent of the composition.

10. A composition of claim 7 wherein the effective amount of the volatile silicone oil is about 22 to about 25 weight percent of the composition.

11. A composition of claim 7 wherein the effective amount of the volatile silicone oil is about 34 to about 36 weight percent of the total composition.

12. A composition of claim 7 which is a liquid.

13. A composition of claim 7 which is a gel.

14. A composition of claim 7 which is a semi-solid.

15. A method of achieving a non-aqueous sunscreen coating having a high SPF value on the skin which comprises applying onto the skin a coating of a non-aqueous sunscreen composition having a high SPF value comprising (a) an effective amount of a volatile silicone oil having a viscosity of no more than about 50 cst in the range of about 20 to about 40 weight percent of the composition sufficient to maintain the SPF of said composition at a value greater than about 20 and (b) non-aqueous sunscreen formulation containing at least one cosmetic emollient, at least one cosmetic wax and an effective sunscreening amount of at least one sunscreening agent and being substantially free of cellulosic film-forming polymers.

16. A method of claim 15 which further comprises incorporating a waterproofing effective amount of a waterproofing agent into said composition.

17. A method of claim 16 wherein said composition contains about 22 to about 36 weight percent of a volatile silicone oil of said composition.

* * * * *